(12) United States Patent
Rossi et al.

(10) Patent No.: US 12,629,323 B2
(45) Date of Patent: May 19, 2026

(54) COSMETIC KIT AND ITS USE AS A MAKE-UP PRODUCT

(71) Applicant: Oxygen Innovation SRL, Padua (IT)

(72) Inventors: Riccardo Rossi, Padua (IT); Daniela Ricci, Padua (IT)

(73) Assignee: Oxygen Innovation SRL, Padua (IT)

( * ) Notice: Subject to any disclaimer, the term of this patent is extended or adjusted under 35 U.S.C. 154(b) by 417 days.

(21) Appl. No.: 17/409,227

(22) Filed: Aug. 23, 2021

(65) Prior Publication Data

US 2021/0378928 A1 Dec. 9, 2021

Related U.S. Application Data

(62) Division of application No. 16/744,555, filed on Jan. 16, 2020, now abandoned.

(30) Foreign Application Priority Data

Mar. 11, 2019 (IT) ........................ 102019000003495

(51) Int. Cl.
| A61K 8/362 | (2006.01) |
| A61K 8/19 | (2006.01) |
| A61Q 1/04 | (2006.01) |
| A61Q 1/10 | (2006.01) |

(52) U.S. Cl.
CPC ................ *A61K 8/362* (2013.01); *A61K 8/19* (2013.01); *A61Q 1/04* (2013.01); *A61Q 1/10* (2013.01); *A61K 2800/43* (2013.01); *A61K 2800/884* (2013.01)

(58) Field of Classification Search
CPC ...... A61K 8/362; A61K 8/19; A61K 2800/43; A61K 2800/884; A61K 2800/95; A61K 8/733; A61Q 1/04; A61Q 1/10
See application file for complete search history.

(56) References Cited

U.S. PATENT DOCUMENTS

| | | | | |
|---|---|---|---|---|
| 2006/0198805 A1* | 9/2006 | Gupta | .................. | A61K 8/0212 424/70.13 |
| 2006/0275233 A1* | 12/2006 | Fishman | .................. | A61K 8/41 424/70.31 |
| 2009/0306163 A1* | 12/2009 | Lipkin | ..................... | A61K 8/49 514/390 |
| 2015/0044263 A1* | 2/2015 | Bibette | .................. | A61Q 19/00 424/401 |

FOREIGN PATENT DOCUMENTS

| | | | |
|---|---|---|---|
| FR | 2949683 | * | 3/2011 |
| JP | 2009541299 | * | 11/2009 |
| KR | 20120023991 | * | 3/2012 |
| KR | 20160101314 A | * | 8/2016 |

* cited by examiner

*Primary Examiner* — Jessica Worsham
(74) *Attorney, Agent, or Firm* — Geoffrey Lottenberg; Berger Singerman LLP

(57) ABSTRACT

A cosmetic kit includes a skin staining composition of (i) a monovalent salt of alginic acid, a water-soluble colorant, and water and (ii) an activating composition of water and a cosmetically acceptable salt of calcium or magnesium. Also disclosed is a method for cosmetically treating or making up the human skin by using the cosmetic kit useful in making up lips, eyelids and eyebrows.

8 Claims, No Drawings

COSMETIC KIT AND ITS USE AS A MAKE-UP PRODUCT

CROSS-REFERENCE TO RELATED APPLICATIONS

This application is a divisional of U.S. patent application Ser. No. 16/744,555 filed on Jan. 16, 2020, which claims the benefit of Italian Patent Application No. 102019000003495 filed on Mar. 11, 2019, the entire contents of which are hereby incorporated by reference.

FIELD OF THE INVENTION

The present invention concerns a cosmetic kit and its use as a make-up product, as well as a cosmetic method for making up human skin, by using the cosmetic kit. In fact, said cosmetic kit finds application especially in making up lips, eyelids and eyebrows.

STATE OF THE ART

It has long been considered desirable to provide cosmetic makeup products, such as lipstick and glosses, which impart a long-lasting shiny or matt finish to skin and particularly to the lips. Conventionally, cosmetic makeup products comprise pigments dispersed in a base of fats or oils with various waxes added to provide the desired consistency of the product. In particular, lip glosses are often liquid to semi-solid in consistency to provide the fluid, smooth consistency and high payoff desired by consumers.

However, the shiny finish and smooth aesthetics provided by the conventional oily base comes at the cost of durability. A significant disadvantage of traditional lip color products is the lack of wear the consumer experiences, resulting in fading, feathering, and diminished gloss, all of which require re-application within a short period of time.

Moreover, lip colors tend to accumulate in fine creases of the lips and surrounding skin leading to an undesirable "feathering" effect. Similarly, the oils may cause the color to migrate or bleed beyond the boundaries of the lips resulting in a halo effect.

To date, efforts to provide durable, long-wearing, lip products have met with only moderate success. Commercial long-wear lip products have been reported to be uncomfortable to wear and may have a drying effect on the lips. Further, the long-lasting shiny finish which is sought in lip gloss products has proven difficult to replicate in such products.

With changing fashion, consumers, who are increasingly demanding, are looking for innovative makeup products that give original or specific make-up effects, but at the same time combine coverage, fluidity, and smooth consistency with wear resistance and vibrant color. It is therefore an object of the present invention to provide cosmetic compositions which meet these requirements and can be used as makeup products.

SUMMARY OF THE INVENTION

The above object has been achieved by a cosmetic kit, as per claim 1.

In another aspect, the invention concerns the cosmetic use of said cosmetic kit as a makeup product.

In a further aspect, the present invention concerns a cosmetic method for making up human skin, by using said cosmetic kit.

In an additional aspect, the present invention concerns a makeup product comprising said cosmetic kit.

The characteristics and the advantages of the present invention will become apparent from the following detailed description and working examples provided for illustrative purposes.

DETAILED DESCRIPTION OF THE INVENTION

The subject of the invention therefore is a cosmetic kit comprising:

(i) a skin staining composition comprising a monovalent salt of alginic acid, a water soluble colorant, and water, wherein the monovalent salt of alginic acid is in an amount up to 10 wt %, based on the weight of composition (i), and (ii) an activating composition comprising water, and a cosmetically acceptable salt of calcium or magnesium.

As it will be widely detailed below and shown in the Examples, the cosmetic kit of the invention allows the skin to be firstly stained upon application of the composition (i), which is soft and spreadable, and then a removable film is formed after application of the composition (ii). Once the film is peeled off, the underlying skin is uniformly and durably colored.

In fact, the cosmetic kit of the invention allows an easy and comfortable makeup of sensitive skin areas such as lips, eyelids or eyebrows, which are face areas typically excluded from facial treatment masks of any kind. Moreover, the very easy and rapid peel-off application results in a tattoo-like makeup, which lasts for hours without smudging or fading.

Alginic acid is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

Commercial varieties of alginic acid salts, or alginates, are extracted from seaweed, including the giant kelp Macrocystis pyrifera, Ascophyllum nodosum, and various types of Laminariaand Lessonia. They are also produced by two bacterial genera Pseudomonas and Azotobacter. The term "monovalent salt of alginic acid" means a salt of alginic acid with monovalent cations.

Preferably, the monovalent salt of alginic acid of composition (i) is sodium alginate, potassium alginate, ammonium alginate, glyceryl alginate, methylsilanol carboxymethyl theophylline alginate, potassium undecylenoyl alginate, propylene glycol alginate, siloxanetriol alginate, sodium alginate sulfate, sodium/TEA-undecylenoyl alginate, TEA-alginate, or a mixture thereof, where TEA is triethanolamine.

In preferred embodiments, the monovalent salt of alginic acid of composition (i) is sodium alginate, potassium alginate, ammonium alginate, or a mixture thereof.

Particularly preferred are those embodiments wherein the monovalent salt of alginic acid of composition (i) is sodium alginate.

Preferably, the monovalent salt of alginic acid is in an amount of 0.1-5 wt %, based on the weight of composition (i), more preferably in an amount of 2-3 wt %.

The skin staining composition (i) also comprises a colorant that is water-soluble. Suitable water-soluble colorants include:

3

| Color | Color labelling in Europe/China-USA-Japan |
| --- | --- |
| Yellow | CI 19140<br>Yellow 5<br>Ki 4 [Yellow 4] |
| Yellow | CI 15985<br>Yellow 6<br>Ki 5 [Yellow 5] |
| Yellow | CI 45350<br>Yellow 8<br>Ki 202-(1) [Yellow 202-(1)] |
| Yellow | CI 10316<br>Ext. Yellow 7<br>Ki 403-(1) [Yellow 403-(1)] |
| Yellow | CI 47005<br>Yellow 10<br>Ki 203 [Yellow 203] |
| Yellow | CI 18965 |
| Orange | CI 15510<br>Orange 4<br>Daidai 205 [Orange 205] |
| Pink | CI 45430 |
| Pink | CI 45100 |
| Red | CI 14700<br>Red 4<br>Aka 504 [Red 504] |
| Red | CI 45380<br>Red 22<br>Aka 230-(1) [Red 230-(1)] |
| Red | C145410<br>Red 28<br>Aka 104-(1) [Red 104-(1)] |
| Red | CI 17200<br>Red 33<br>Aka 227 [Red 227] |
| Red | CI 16035<br>Red 40 |
| Red | CI 16255<br>Aka 102 [Red 102] |
| Red | CI 14720 |
| Red | CI 16185 |
| Brown | CI 14700/CI 19140/CI 17200<br>D&C Brown n°1 Replacement<br>Red 504/Yellow 4/Red 227 |
| Violet | CI 60730<br>Ext. Violet 2<br>Murasaki 401 [Violet 401] |
| Violet | CI 45100/CI 18965 |
| Blue | CI 42090<br>Blue 1<br>Ao 1 [Blue 1] |
| Blue | CI 42051 |
| Blue | CI 42090 |
| Blue | CI 74180 |
| Green | CI 42053<br>Green 3<br>Midori 3 [Green 3] |
| Green | CI 61570<br>Green 5<br>Midori 201 [Green 201] |
| Green | CI 59040<br>Green 8<br>Midori 204 [Green 204] |
| Green | CI 42090/CI 19140 |
| Green | CI 19140/CI 42051 |
| Green | CI 47005/CI 74180 |
| Green | CI 19140/CI 42051 |
| Green | CI 19140/CI 42090 |
| Green | CI 45350 |
| Green | CI 42090/CI 45350 |
| Green | CI 10020 |
| Black | CI 28440 |

In the table above, "CI" stands for "color index". The color indexes are 5-digit numbers grouped into numerical ranges according to the chemical structure of the colorants (both dyes and pigments), as per the Color Index International, which is a reference database jointly maintained by the Society of Dyers and Colorists and the American Association of Textile Chemists and Colorists.

The table includes colors of single colorants as well as colors being mixtures of colorants.

Preferably, the water-soluble colorant of the present invention is a colorant listed in the table above or a mixture thereof.

Preferably, the water-soluble colorant is in an amount up to 3 wt %, based on the weight of composition (i), more preferably in an amount of 0.01-2 wt %.

Particularly preferred are those embodiments wherein the water-soluble colorant is in an amount of 0.1-0.3 wt %, based on the weight of composition (i).

Preferably, in composition (i), water is in an amount of at least 65 wt %, more preferably up to 70 wt %, based on the weight of composition (i).

In preferred embodiments, the cosmetically acceptable salt of calcium or magnesium of composition (ii) is calcium chloride, calcium bromide, calcium nitrate, calcium citrate, calcium formate, calcium acetate, calcium gluconate, calcium ascorbate, calcium lactate, calcium glycinate, calcium aspartate, calcium carbonate, calcium malate, calcium dihydrogen phosphate, calcium glycerophosphate, calcium PCA, calcium phosphate, calcium salicylate, calcium sorbate, calcium sulphate, calcium tartrate, dicalcium phosphate, tricalcium phosphate, calcium hydroxyapatite, calcium behenate, calcium laurate, calcium myristate, calcium propionate, calcium stearate, calcium stearoyl lactylate, calcium undecylenate, magnesium chloride, magnesium bromide, magnesium nitrate, magnesium citrate, magnesium formate, magnesium acetate, magnesium gluconate, magnesium ascorbate, magnesium ascorbyl phosphate, magnesium lactate, magnesium glycinate, magnesium aspartate, magnesium carbonate, magnesium malate, magnesium PCA, magnesium salicylate, magnesium sorbate, magnesium sulphate, magnesium tartrate, magnesium behenate, magnesium laurate, magnesium myristate, magnesium propionate, magnesium stearate, magnesium stearoyl lactylate, magnesium undecylenate, or a mixture thereof.

In particularly preferred embodiments, the cosmetically acceptable salt of calcium or magnesium of composition (ii) is calcium chloride, calcium citrate, calcium acetate, calcium phosphate, dicalcium phosphate, magnesium chloride, magnesium citrate, magnesium lactate, magnesium sulphate, or a mixture thereof.

Preferably, the cosmetically acceptable salt of calcium or magnesium is in an amount up to 70 wt %, based on the weight of composition (ii), more preferably in an amount of 2-50 wt %.

Particularly preferred are those embodiments wherein the cosmetically acceptable salt of calcium or magnesium is in an amount of 2-20 wt %, based on the weight of composition (ii).

In preferred embodiments of the cosmetic kit of the present invention, the cosmetically acceptable salt of calcium or magnesium is in an amount so that calcium or magnesium cations are at least stoichiometric with the alginate anions of the monovalent salt of alginic acid.

Preferably, in composition (ii), water is in an amount of at least 80 wt %, more preferably at least 85 wt %, based on the weight of composition (ii).

The skin staining composition (i) and the activating composition (ii) of the cosmetic kit can also comprise cosmetically acceptable additives, such as flavoring agents, botanical extracts, anti-microbial agents, anti-irritants agents, chelating agents, preservatives, pH adjusters, humectants, vitamins, antioxidants, fragrances, stabilizers, solvents, moisturizers, UV absorbers, and mixtures thereof.

For the purposes of the present invention, said cosmetically acceptable additives do not interfere as such or are not in an amount so as to interfere with the action of the essential components of compositions (i) and (ii) and can be mixed therewith.

Non-limiting examples of moisturizers and humectants that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, xylitol, acetylated lanolin, acetylated lanolin alcohol, alanine, algae extract, aloe barbadensis, aloe-barbadensis extract, aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, *Anadenanthera colubrina* bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, *Cardamon* (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated cocoglycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, *Matricaria* (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, butylen glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum park(ii)*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

Non-limiting examples of flavoring agents that can be used with the compositions of the present invention include aromas and sweeteners, such as gluconate, aspartame, cyclamate, saccharin sodium, xylitol, sucralose, and maltitol.

Non-limiting examples of stabilizers that can be used with the compositions of the present invention include hydroxyethyl acrylate/sodium acryloyldimethyl taurate copolymer, squalene, polysorbate 60, and mixtures thereof.

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbital furfural, thiodiglycol, thiodiglycolamide, thiodigly-colic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicoti-nate, tocopheryl succinate, and tris(nonylphenyl)phosphite.

Non-limiting examples of preservatives that can be used in the context of the present invention include phenoxyetha-nol, ethylhexylglycerin 1,2-hexandiol, caprylyl glycol, ben-zyl alcohol, chlorobutanol, phenol, sorbic acid, thimerosal or combinations thereof.

In Preferred Embodiments, the Cosmetic Kit of the Present Invention Comprises:

(i) a skin staining composition comprising 0.1-5 wt % of a monovalent salt of alginic acid, up to 3 wt % of a water-soluble colorant, based on the weight of compo-sition (i), and water, and (ii) an activating composition comprising water, and up to 70 wt % a cosmetically acceptable salt of calcium or magnesium, based on the weight of composition (ii).

In More Preferred Embodiments, the Cosmetic Kit of the Present Invention Comprises:

(i) a skin staining composition comprising 2-3 wt % of a monovalent salt of alginic acid, 0.01-2 wt % of a water-soluble colorant, based on the weight of compo-sition (i), and water, and (ii) an activating composition comprising water, and 2-50 wt % a cosmetically acceptable salt of calcium or magnesium, based on the weight of composition (ii).

Particularly Preferred are Those Embodiments, Wherein the Cosmetic Kit of the Present Invention Comprises:

(i) a skin staining composition comprising 2-3 wt % of a monovalent salt of alginic acid, 0.1-0.3 wt % of a water-soluble colorant, based on the weight of compo-sition (i), and water, and (ii) an activating composition comprising water, and 2-20 wt % a cosmetically acceptable salt of calcium or magnesium, based on the weight of composition (ii), wherein said monovalent salt of alginic acid of com-position (i) is sodium alginate, potassium alginate, ammonium alginate, or a mixture thereof, and wherein said cosmetically acceptable salt of calcium or magne-sium is calcium chloride, calcium citrate, calcium acetate, calcium phosphate, dicalcium phosphate, mag-nesium chloride, magnesium citrate, magnesium lac-tate, magnesium sulphate or a mixture thereof.

In Certain Embodiments, the Cosmetic Kit of the Invention Consists Essentially of:

(i) a skin staining composition comprising a monovalent salt of alginic acid, a water-soluble colorant, and water, wherein the monovalent salt of alginic acid is in an amount up to 10 wt %, based on the weight of com-position (i), and (ii) an activating composition comprising water, and a cosmetically acceptable salt of calcium or magnesium.

The expression "consists essentially of" means that the monovalent salt of alginic acid, water-soluble colorant, and cosmetically acceptable salt of calcium or magnesium are the only ingredients present in the composition of the invention which play an active role in staining skin, while any other components or additives do not interfere as such or are not in an amount so as to interfere with the action of the essential components of compositions (i) and (ii) and can be mixed therewith.

In Other Embodiments, the Composition of the Invention Consists of:

(i) a skin staining composition comprising a monovalent salt of alginic acid, a water-soluble colorant, water, and cosmetically acceptable additives, wherein the mon-ovalent salt of alginic acid is in an amount up to 10 wt %, based on the weight of composition (i), and (ii) an activating composition comprising water, a cos-metically acceptable salt of calcium or magnesium, and cosmetically acceptable additives.

All the compositions described above can be prepared by methods known in the cosmetic field, e.g. by adding and mixing the components and/or additives.

In another aspect, the invention concerns the cosmetic use of said cosmetic kit as a makeup product.

Preferably, said cosmetic kit is used for making up lips, eyelids and eyebrows, by uniformly and durably staining the corresponding skin areas with the water-soluble colorant.

In an additional aspect, the present invention concerns a makeup product comprising said cosmetic kit.

Said makeup product can comprise a first container wherein composition (i) is contained, and a second container wherein composition (ii) is contained.

Preferably, the first container is provided with a releasable applicator for applying the composition (i) on the skin area to be stained, said applicator preferably having a brush tip, a spatula tip, or a sponge tip.

Preferably, the second container is a dispenser having a spray pump assembly with an outlet nozzle, an inlet fluid passage channel, and a manually actuable pump trigger, the spray pump assembly being coupled to the dispenser body.

In a further aspect, the present invention concerns a cosmetic method for making up human skin, by using said cosmetic kit.

Particularly, Said Cosmetic Method Comprises the Follow-ing Steps:

1) applying the skin staining composition (i) on the skin area to be stained, 2) applying the activating composition (ii) on the com-position (i), thus forming a film, and 3) removing the film by peeling it off from the stained skin.

In step 1), the composition (i) comprising a monovalent salt of alginic acid, a water-soluble colorant, and water, is applied onto the skin area to be stained. Preferably, the composition (i) is applied onto lips, eyelids or eyebrows. In fact, it should be appreciated that the components of com-position (i), as well as the components of composition (ii), are suitable for these delicate and sensitive skin areas, as they do not trigger any adverse reaction or dehydrating process.

Once the composition (i) is applied, the colorant transfers on the epidermis, owing to its water-solubility property, and stains the skin.

The composition (ii) is preferably applied on composition (i), without waiting for the latter being dried. In this way, in step 2), the acidic groups of L-guluronic acid (G) and D-mannuronic acid (M) of the alginic backbone are com-pletely ionized in water and a gel forms instantly when divalent ions, i.e. calcium and/or magnesium, present in the aqueous composition (ii) are added. This explains why the salt of alginic acid is monovalent, irrespective of the cation selected, and the composition (ii) comprises divalent cations, i.e. calcium or magnesium, irrespective of the anion selected.

The guluronic acid is a negative charged (1-4) α-L-guluronate, which interacts with the positive charged ions. Divalent ions, such as calcium or magnesium, cross link the molecules into a strong three-dimensional network. The α linkage between the molecules orient the molecules into "hills" and "valleys". The divalent ion links the "valley" from one molecule to the "valley" from the other molecule causing the alginate to gel.

The mannuronic acid is a negative charged (1-4) β-D-mannurate, interacting as well as the guluronic acid with other ions, but to a much lesser degree. The β linkage creates a more linear molecule without "hills" and "valleys". This explains in part why the resulting alginate type has soft and elastic gel properties.

Therefore, for the purposes of the present invention, alginates rich in guluronic acids are preferred, as they form stronger and more cohesive gels than alginates rich in mannuronic acid.

After no more than few seconds, preferably 3-10 seconds, and more preferably about 5 seconds, the film formed in step 2) can be easily peeled off, thus leaving the underlying skin perfectly stained with a rich and vibrant color that lasts all day long, without smudging or fading.

Moreover, no film residues remain on skin during or after removal, so that the underlying skin is not only uniformly colored, but also pleasantly clean and moisturized.

Optionally, a top coat can be applied, e.g. a transparent gloss, if the colored area is lips. From what above disclosed, it is clear that the cosmetic kit of the invention allows an easy and comfortable makeup of sensitive skin areas such as lips, eyelids or eyebrows, which are face areas typically excluded from facial treatment masks of any kind.

Moreover, the very easy and rapid peel-off application results in a tattoo-like makeup, which lasts for hours without smudging or fading.

It should be also understood that all the combinations of preferred aspects of the cosmetic kit of the invention, as well as of the preparation, and the uses of the same, as above reported, are to be deemed as hereby disclosed.

All combinations of the preferred aspects of the cosmetic kit of the invention, the preparation, and the uses disclosed above are to be understood as herein described.

Below are working examples of the present invention provided for illustrative purposes.

EXAMPLES

Example 1

The Following Composition (i) has been Prepared:

| Component (INCI name) | wt % |
|---|---|
| Sodium alginate (Algin) | 2% |
| Water | 79.35% |
| Red 28 | |
| CI45410 | |
| Pentylene Glycol | 5% |
| Glycerin | 2% |
| Butylen Glycol | 3% |
| Hydroxyethyl Acrylate/Sodium Acryloyldimethyl TaurateCopolymer | 1% |

-continued

| Component (INCI name) | wt % |
|---|---|
| (and) Water/Aqua (and) Squalane (and) Polysorbate 60 | |
| 1,2-Hexanediol (and) Caprylyl Glycol | 1% |
| Lactic Acid (and) Water/Aqua | 0.25% |
| Flavor | 0.1% |
| Caprylyl/capryl glucoside, Polyglyceryl-10 isostearate Sodium dilauramidoglutamide lysine | 0.1% |
| Mica, Tin oxide, Titanium Dioxide, Indigofera Tinctoria Leaf Extract | 6% |

The Following Composition (ii) has been Prepared:

| Component (INCI name) | wt % |
|---|---|
| Water | 93.20% |
| Calcium Chloride | 5% |
| Sodium Saccharin | 0.3% |
| Phenoxyethanol (and) Ethylhexylglycerin | 1% |
| Water (and) Glycerin (and) Anadenanthera Colubrina Bark Extract | 0.5% |

The composition (i) has been applied on the lips of 25 volunteers. Composition (ii) has been sprayed twice directly on the lips.

Then the film formed thereon has been peeled off from the lips corner inwards, without letting it dry.

For all the volunteers, the result was a satisfactory quick and easy makeup, and a vibrant color that lasted on lips for hours, without smudging or fading.

Example 2

The Following Composition (i) has been Prepared:

| Component (INCI name) | wt % |
|---|---|
| Sodium alginate (Algin) | 2% |
| Water | 79.35% |
| Red 33 | 0.1% |
| CI 17200 | |
| Pentylene Glycol | 5% |
| Glycerin | 2% |
| Butylen Glycol | 3% |
| Hydroxyethyl Acrylate/Sodium Acryloyldimethyl TaurateCopolymer | 1% |
| (and) Water/Aqua (and) Squalane (and) Polysorbate 60 | |
| 1,2-Hexanediol (and) Caprylyl Glycol | 1% |
| Lactic Acid (and) Water/Aqua | 0.25% |
| Flavor | 0.1% |
| Caprylyl/capryl glucoside, Polyglyceryl-10 isostearate Sodium dilauramidoglutamide lysine | 0.1% |
| Mica, Tin oxide, Titanium Dioxide, Indigofera Tinctoria Leaf Extract | 6.1% |

The Following Composition (ii) has been Prepared:

| Component (INCI name) | wt % |
|---|---|
| Water | 93.20% |
| Calcium Chloride | 5% |
| Sodium Saccharin | 0.3% |
| Phenoxyethanol (and) Ethylhexylglycerin | 1% |
| Water (and) Glycerin (and) Anadenanthera Colubrina Bark Extract | 0.5% |

The composition (i) has been applied on the lips of 25 volunteers. Composition (ii) has been sprayed twice directly on the lips.

Then the film formed thereon has been peeled off from the lips corner inwards, without letting it dry.

For all the volunteers, the result was a satisfactory quick and easy makeup, and a vibrant color that lasted on lips for hours, without smudging or fading.

Example 3

The Following Composition (i) has been Prepared:

| Component (INCI name) | wt % |
|---|---|
| Sodium alginate (Algin) | 2% |
| Water | 79.35% |
| Red 33 | 0.2% |
| CI 17200 | |
| Pentylene Glycol | 5% |
| Glycerin | 2% |
| Butylen Glycol | 3% |
| Hydroxyethyl Acrylate/Sodium | 1% |
| Acryloyldimethyl Taurate Copolymer | |
| (and) Water/Aqua (and) Squalane | |
| (and) Polysorbate 60 | |
| 1,2-Hexanediol (and) Caprylyl Glycol | 1% |
| Lactic Acid (and) Water/Aqua | 0.25% |
| Flavor | 0.1% |
| Caprylyl/capryl glucoside, | 0.1% |
| Polyglyceryl-10 isostearate Sodium | |
| dilauramidoglutamide lysine | |
| Mica CI 77019 (and) Titanium | 6.0% |
| Dioxide CI 77891 (and) Tin Oxide | |

The Following Composition (ii) has been Prepared:

| Component (INCI name) | wt % |
|---|---|
| Water | 93.20% |
| Magnesium Chloride | 5% |
| Sodium Saccharin | 0.3% |
| Phenoxyethanol (and) Ethylhexylglycerin | 1% |
| Water (and) Glycerin (and) Anadenanthera | 0.5% |
| Colubrina Bark Extract | |

The composition (i) has been applied on the lips of 25 volunteers. Composition (ii) has been sprayed twice directly on the lips.

Then the film formed thereon has been peeled off from the lips corner inwards, without letting it dry.

For all the volunteers, the result was a satisfactory quick and easy makeup, and a vibrant color that lasted on lips for hours, without smudging or fading.

Example 4

The Following Composition (i) has been Prepared:

| Component (INCI name) | wt % |
|---|---|
| Potassium alginate | 2% |
| Water | 79.35% |
| Red 28 | 0.2% |
| CI 45410 | |
| Pentylene Glycol | 5% |
| Glycerin | 2% |
| Butylen Glycol | 3% |
| Hydroxyethyl Acrylate/Sodium | 1% |
| Acryloyldimethyl Taurate Copolymer | |

-continued

| Component (INCI name) | wt % |
|---|---|
| (and) Water/Aqua (and) Squalane | |
| (and) Polysorbate 60 | |
| 1,2-Hexanediol (and) Caprylyl Glycol | 1% |
| Lactic Acid (and) Water/Aqua | 0.25% |
| Flavor | 0.1% |
| Caprylyl/capryl glucoside, | 0.1 |
| Polyglyceryl-10 isostearate Sodium | |
| dilauramidoglutamide lysine | |
| Mica, Tin oxide, Titanium Dioxide, | 3.0% |
| Indigofera Tinctoria Leaf Extract | |
| Mica CI 77019 (and) Titanium | 3.0% |
| Dioxide CI 77891 (and) Iron Oxides | |
| CI 77491 | |

The Following Composition (ii) has been Prepared:

| Component (INCI name) | wt % |
|---|---|
| Water | 93.20% |
| Magnesium Chloride | 5% |
| Sodium Saccharin | 0.3% |
| Phenoxyethanol (and) Ethylhexylglycerin | 1% |
| Water (and) Glycerin (and) Anadenanthera | 0.5% |
| Colubrina Bark Extract | |

The composition (i) has been applied on the lips of 25 volunteers. Composition (ii) has been sprayed twice directly on the lips.

Then the film formed thereon has been peeled off from the lips corner inwards, without letting it dry.

For all the volunteers, the result was a satisfactory quick and easy makeup, and a vibrant color that lasted on lips for hours, without smudging or fading.

The invention claimed is:

1. A cosmetic method for making up human lips, comprising:
   a. providing a cosmetic kit having (i) a lips staining composition comprising a monovalent salt of alginic acid, an effective amount of a water-soluble colorant to visibly stain the lips, and water, wherein the monovalent salt of alginic acid is in an amount up to 10 wt. %, based on the weight of composition (i), and (ii) an activating composition comprising water, and a cosmetically acceptable salt of calcium or magnesium;
   b. in a first step, applying the lips staining composition (i) on the lip area to be stained;
   c. in a second step, spraying the activating composition (ii) on the composition (i), thereby forming a film on the lips; and
   d. in a third step, removing the film by peeling it off from the stained lips, leaving behind smudge and fade resistant stained lips wherein the third step is performed after the composition (ii) is sprayed onto composition (i) and left on for up to 10 seconds.

2. The method of claim 1, wherein the monovalent salt of alginic acid of composition (i) is sodium alginate, potassium alginate, ammonium alginate, or a mixture thereof.

3. The method of claim 2, wherein the monovalent salt of alginic acid is within a range of 0.1-5 wt. %, based on the weight of composition (i).

4. The method of claim 3, wherein the water-soluble lips staining colorant is within a range of 0.2-3 wt. %, based on the weight of composition (i).

5. The method of claim 4, wherein the cosmetically acceptable salt of calcium or magnesium of composition (ii)

is calcium chloride, calcium citrate, calcium acetate, calcium phosphate, dicalcium phosphate, magnesium chloride, magnesium citrate, magnesium lactate, magnesium sulphate or a mixture thereof.

6. The method of claim 5, wherein the cosmetically acceptable salt of calcium or magnesium is within a range of 2-70 wt. %, based on the weight of composition (ii).

7. The method of claim 1, wherein anions of the monovalent salt of alginic acid of lips staining composition (i) bind with cations of the salt of calcium or magnesium of activating composition (ii) to form a crosslinked network.

8. A cosmetic method for making up human lips, comprising:

a. providing a cosmetic kit having a first container having a removable applicator with an applicator tip, the first container retaining (i) a lips staining composition comprising a monovalent salt of alginic acid, an effective amount of a water-soluble colorant to visibly stain the lip, and water, wherein the monovalent salt of alginic acid is in an amount up to 10 wt. %, based on the weight of composition (i), and a dispenser with a spray pump assembly that includes a spray nozzle, the dispenser retaining (ii) an activating composition comprising water, and a cosmetically acceptable salt of calcium or magnesium;

b. in a first step, applying the lips staining composition (i) on the lip area to be stained with the applicator tip that is configured to make contact with the lips;

c. in a second step, spraying via the spray nozzle the activating composition (ii) on the composition (i), thereby forming a film on the lips; and d. in a third step, removing the film by peeling it off from the stained lips, leaving behind smudge and fade resistant stained lips wherein the third step is performed after the composition (ii) is sprayed onto composition (i) and left on for up to 10 seconds.

\*   \*   \*   \*   \*